United States Patent [19]

Laubscher

[11] Patent Number: 5,054,317
[45] Date of Patent: Oct. 8, 1991

[54] DEVICE FOR MONITORING AND/OR MEASURING PARAMETERS OF A RUNNING, THREAD-LIKE OR WIRE-LIKE TEST MATERIAL AND METHOD FOR OPERATING THE DEVICE

[75] Inventor: Hanspeter Laubscher, Gossau, Switzerland

[73] Assignee: Zellweger Uster AG, Uster, Switzerland

[21] Appl. No.: 536,157

[22] Filed: Jun. 7, 1990

[30] Foreign Application Priority Data

Jun. 7, 1989 [CH] Switzerland .............. 02139/89

[51] Int. Cl.$^5$ .............. G01B 7/32; G01B 11/10; G01B 7/08
[52] U.S. Cl. .............. 73/160; 250/561; 250/571; 324/671; 356/238; 356/429; 356/430
[58] Field of Search .............. 73/160; 340/677; 356/429, 430, 238; 324/663, 671; 250/560, 561, 571, 572

[56] References Cited

U.S. PATENT DOCUMENTS

| | | | |
|---|---|---|---|
| 2,516,768 | 7/1950 | Grob et al. | 324/672 |
| 3,039,051 | 6/1962 | Locher | 73/160 |
| 3,922,601 | 11/1975 | Martin, Jr. | 73/160 |
| 4,184,770 | 1/1980 | Pinior | 356/430 |
| 4,233,520 | 11/1980 | Canfield | 356/238 |
| 4,294,545 | 10/1981 | Stutz | 356/429 |
| 4,511,253 | 4/1985 | Glockner et al. | 356/385 |
| 4,610,707 | 9/1986 | Grundy | 73/160 |
| 4,706,014 | 11/1987 | Fabbri | 73/160 |

OTHER PUBLICATIONS

"Electronics and Computers", Second Edition, by Sybil P. Parker McGraw-Hill Company, 1988, pp. 324-325.
Philips Technical Publication No. 260, "Liquid Crystal Displays. . . Principles and Applications," (Aug. 1988).

Primary Examiner—Allan N. Shoap
Assistant Examiner—Diego F. F. Gutierrez
Attorney, Agent, or Firm—Burns, Doane, Swecker & Mathis

[57] ABSTRACT

The device contains a measuring gap, which is provided for the passage of the test material, the measuring gap having two side walls each of which is provided with a measuring electrode forming part of a capacitive measuring element. An optical measuring element having a light source arranged on one side of the measuring gap and having a photoelectric element is provided in addition to the capacitive measuring element, and both measuring elements form part of a common measuring head. The fluctuations in accuracy of previous measuring heads having only one measuring element are thereby reduced and automatic checking of the measuring head output can be preformed. In addition, parameters which could not be determined with previous measuring heads can be measured and monitored in accordance with the present invention.

13 Claims, 2 Drawing Sheets

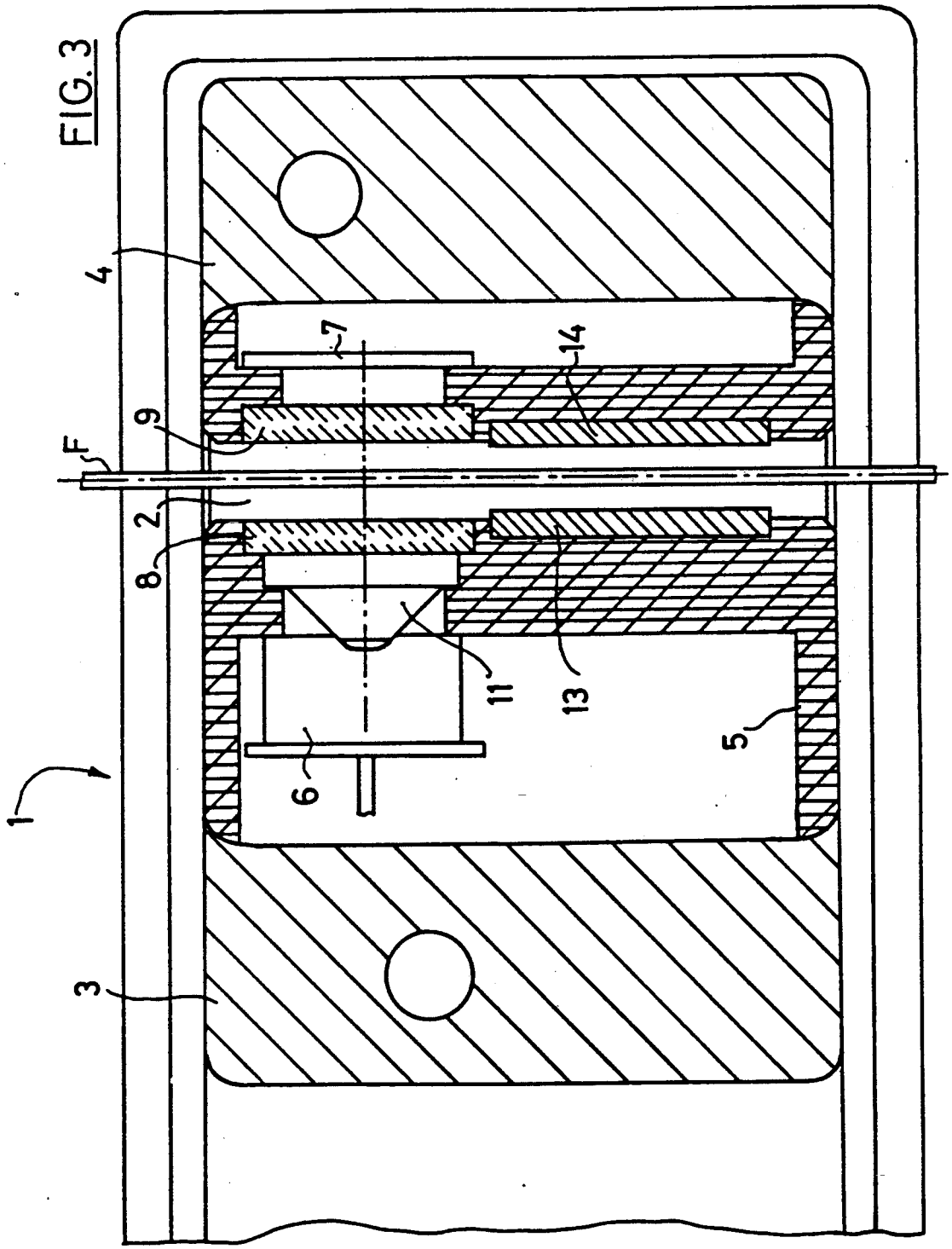

DEVICE FOR MONITORING AND/OR MEASURING PARAMETERS OF A RUNNING, THREAD-LIKE OR WIRE-LIKE TEST MATERIAL AND METHOD FOR OPERATING THE DEVICE

BACKGROUND OF THE INVENTION

The present invention relates to a device for monitoring and/or measuring parameters of a running, thread-like or wire-like test material, having a measuring gap which is provided for the passage of the test material and on each of the two side walls of which is provided a measuring electrode forming part of a capacitive measuring element.

There are now millions of devices of this kind which are based on the capacitive measuring principle, such as so-called electronic yarn clearers, on the one hand, and uniformity testers on the other hand. The electronic yarn clearers, such as the USTER AUTOMATIC type from Zellweger Uster AG, serve to detect troublesome yarn defects, including, for example, short thickenings, thinnings and frequent thickenings and thinnings (Moire). Uniformity testers such as the USTER TESTER from Zellweger Uster AG (USTER is a registered trademark of Zellweger Uster AG) serve to detect and analyze fluctuations in the weight per unit length of slivers, rovings and yarns.

Due to its high measuring accuracy and its constant sensitivity for many years, the capacitive measuring principle has become very widespread. In addition to the devices based on this principle, optical measuring heads are also used, with which the diameter of the test material can be determined. These optical measuring heads are used in particular when capacitive measuring heads cannot be employed. This is the case, for example, with the testing of electrically conductive yarns.

Irrespective of the type of measuring principle used, the measuring heads are dependent to a certain extent, due to their principle of operation and their construction, on extraneous influences, such as, for example, moisture, shape of the yarn cross-section, position of dependency, influence of the material, etc., which cannot be eliminated or reduced using the technology available although there would be great interest in doing so. A further, as yet unsolved problem is a universal measuring head usable for all types of yarns with all the advantages of the capacitive measuring principle. Finally, with increasing automation, it would also be desirable if a type of self-checking measuring head were available.

SUMMARY OF THE INVENTION

The invention is intended to achieve all these objects. The intention is thus to specify a measuring head which is less dependent on extraneous influences than the known measuring heads, which can be employed universally and which checks itself.

These objects are achieved according to the invention by providing an optical measuring element having a light source arranged on one side of the measuring gap and having a photoelectric element in addition to the capacitive measuring element, and both measuring elements form part of a common measuring head.

Practical tests have shown that the two measuring elements cooperate in such a way that the dependence on extraneous influences and fluctuations in accuracy caused thereby are reduced in relation to the known measuring heads. The universal applicability of the measuring heads according to the invention is evident and the automatic checking strived for is achieved by interpreting deviations between the results supplied by the two measuring elements to detect faulty operation by one of the two measuring elements.

Over and above the qualities mentioned, the measuring head according to the invention furthermore has the additional advantage that it permits the online measurement and monitoring of parameters which it was hitherto not possible to monitor or at least not in such a simple way. Thus, in addition to the usually monitored parameters, cross-section and diameter, it is additionally possible, for example, for bulk, hairiness and moisture content to be monitored and measured. A further interesting and hitherto impossible advantage of the present invention arises from the combined evaluation of the values of the two measuring elements: as is known, the capacitive measuring element measures the variation in cross-section or, more precisely, the weight of the test material per unit length, and the optical measuring element measures the diameter. The combination of the two types of measured values provides information on the weight per unit volume, i.e. a variable comparable with the physical density. From this, it is in turn possible to draw conclusions about other variables, such as, for example, the yarn twist.

From this illustrative and in no way definitive list it can be seen that the measuring head according to the invention has a number of unexpected qualities and, in particular, permits the measurement and monitoring of parameters which it was hitherto impossible to measure using the known, simple measuring heads, whether these were capacitive or optical.

The invention furthermore relates to a method for operating the inventive device. This method is characterized by effecting a matching of the two measuring elements to the same sensitivity.

BRIEF DESCRIPTION OF THE DRAWINGS

Other objects and advantages of the present invention will become more apparent from the following detailed description of preferred embodiments as described in conjunction with the accompanying drawings in which:

FIG. 3 shows a sectional representation of a third illustrative embodiment of a device according to the invention, with the sectional plane being in the plane of a running thread and transverse to a measuring gap of the device.

DETAILED DESCRIPTION OF PREFERRED EMBODIMENTS

Figure 1:
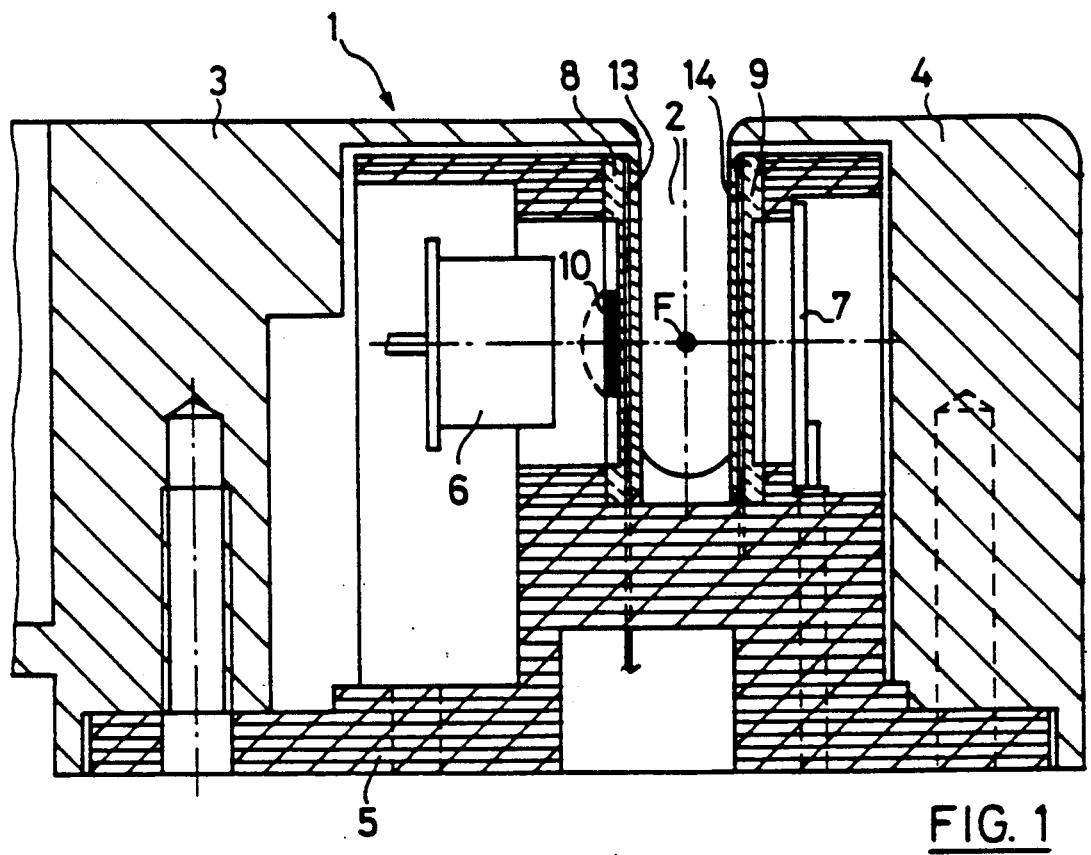
FIG. 1 shows a sectional representation of a first illustrative embodiment of a device according to the invention with the section plane transverse to the direction of thread running.

The preferred embodiments of devices in accordance with the present invention, as illustrated in the Figures, are used to monitor and/or measure parameters of, for example, running threads, in particular for both the optical and capacitive acquisition of their diameter and cross-section. Each of these devices, which are also referred to as measuring heads, has a housing 1 with a measuring gap 2 through which the thread F to be measured runs. In this context, thread denotes an elongate test material such as a thread or yarn or a textile ribbon or even a wire. The illustrative embodiments are in each case, on an enlarged scale of about 5:1; in the illustrative embodiment represented in FIG. 2, the measuring gap 2 is wider than in the illustrative embodiments of FIGS. 1 and 3.

The housing 1, which is injection-moulded in one piece from plastic, is in the form of a box with an open base. It is divided into two halves 3 and 4 by a recess for the measuring gap 2. A carrier plate 5 for the optical and electronic components of the device is inserted into the open housing base and screwed to the housing 1.

Arranged on the carrier plate 5 in the region of the left-hand half 3 of the housing in the Figures is a light source 6, preferably a light-emitting diode, which emits light onto a photodiode 7 arranged in the region of the right-hand half 4 of the housing. The measuring gap 2 is screened from the light-emitting diode 6 and from the photodiode 7 by diffusing screens 8 and 9 respectively, a diffuse illumination thereby being produced in the measuring gap 2, also impinging on the photodiode 7 as diffuse light. The diffusing screen 9 in front of the photodiode 7 can also be designed as a filter plate for screening out the ambient light or it can simultaneously serve as a diffusing screen and as a filter plate.

If a thread F running through the measuring gap 2 exhibits a change in cross-section due to a yarn defect, for example a thickening or thinning, the shading of the photodiode 7 changes and, accordingly, the output signal of the photodiode changes. Using this change in the output signal of the photodiode 7, it is then possible either simply to record the defect as such or to halt the running thread F and eliminate the defect.

To achieve a homogeneous field of illumination in the measuring gap 2, a diaphragm 10 (FIG. 1) or a frustoconical light guide 11 having a recess 12 (FIGS. 2 and 3) is provided between the light-emitting diode 6 and the diffusing screen 8. These elements are not explained further here; reference is made in this context to EP-A-244,788, the disclosure of which is hereby incorporated by reference in its entirety, where the optical part of a measuring head as represented in the Figures of the present invention is described in detail.

As can be seen from the Figures, a so-called capacitive measuring element is provided in addition to the optical measuring element described thus far, the individual figures showing different possibilities for the arrangement of the capacitive measuring element relative to the optical measuring element. Measuring heads having capacitive measuring elements have been available worldwide for decades in the electronic yarn clearers USTER AUTOMATIC and in the uniformity testers USTER TESTER of Zellweger Uster AG and are therefore considered to be known. U.S. Pat. Nos. 2,516,768 and 3,009,101 are but two of the large number of patents relating to measuring heads of this kind, and their disclosures are hereby incorporated by reference in their entirety.

Figure 2:
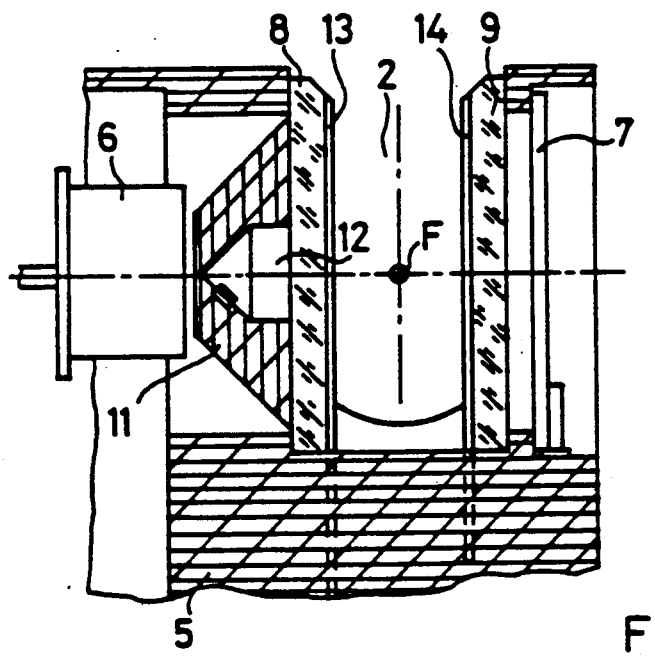
FIG. 2 shows a detailed variant of a second illustrative embodiment of FIG. 1.

In the Figures of the present invention, the capacitive measuring element is symbolized by two capacitor plates 13, 14; a detailed illustration has been omitted due to the known existence of the capacitive measuring principle. FIGS. 1 and 2 each show an arrangement in which the measuring zones of the optical and of the capacitive measuring elements coincide; in the illustrative embodiment of FIG. 3, these measuring zones are arranged adjacent to one another.

According to FIG. 1, the capacitor plates 13 and 14 represent measuring electrodes of lattice like or sievelike design, and are each formed by an electrically conductive metal or plastic layer which is embedded in the diffusing screens 8 and 9 and is "transparent" for the optical measuring element. Each diffusing screen can be of sandwich-like design and the electrically conductive metal or plastic layer can be applied as a film-like metal layer to one part of each diffusing screen by spraying or by vapor deposition or by atomizing (so-called sputtering on). Alternately, layers forming the capacitor plates 13, 14 could, for example, be formed by a fine-meshed network of a suitable material, such as, for example, metal.

In the illustrative embodiment of FIG. 2, the layers forming the capacitor plates 13, 14 are not embedded in the diffusing screens 8, 9; rather the diffusing screens are coated on one side with the respective layers. This side can be the side facing the thread F, as illustrated in the Figure, but can in principle also be the side facing away from the thread F. The remarks made in connection with FIG. 1 apply to the design of the layers and their material in FIG. 2.

FIG. 3 shows an illustrative embodiment in which the optical and the capacitive measuring element do not have a common measuring zone, but rather, have spatially separated measuring zones. According to the exemplary embodiment of FIG. 3, the measuring zones and thus also the measuring elements are arranged one behind the other in the thread running direction. In this embodiment, the two measuring elements are completely independent of one another.

Although, with the measuring head represented in FIG. 3, the capacitive and the optical measurement are not effected at the same point in time on the same elements of the thread but on adjoining elements, this difference between the signals of the two measurements can be compensated in the signal processing. The compensation can, for example, be effected by delaying the signals of the measuring element to the rear in the thread running direction, the measuring zone of which is entered by each part of the thread F earlier than that of the measuring element at the front in the thread running direction, by an amount of time required for a point on the thread to pass from the rear measuring element to the front measuring element. For certain applications, however, the difference between the signals of the two measurements will not be troublesome, with the result that this difference need not be compensated.

Since the two measuring systems, the capacitive and the optical, will generally have a different sensitivity, they must be matched to the same sensitivity. This is preferably done automatically before the start of a measurement, by, for example, correlation or similar methods, with or without the static signal component.

In accordance with the present invention, a relatively accurate composite signal is produced using a sum of the signals from the two measuring systems, and preferably by averaging both of these signals. More specifically, the composite signal is produced after signal reshaping and filtering in the time or frequency domain has been carried out to suppress the more unfavorable extraneous influences in each of the two signals (i.e., to produce a composite signal, the two signals should be reshaped to equal frequency and linearity conditions). Upon insertion of the thread, the zero point of the two measuring elements is matched. Drift is corrected by using the measuring element known to be more stable for a given measurement, and in those cases where the moisture can vary, the amplification is derived from the optical measuring element. Irregularities in the running thread F, such as thickenings, thinnings and the like, are determined by averaging the signals of the two measuring elements. Burls ar detected from the signals of the optical measuring element via filtering in the time or frequency domain.

In accordance with yet another feature of the present invention, signals from the two measuring systems can be evaluated to detect changes in extraneous influences. To detect a change in extraneous influences, it is not the sum but the difference of the two measurement signals which is formed, after selective amplification of the extraneous influences. For example, to measure moisture content, the signals from the two measuring systems must be amplified so that the difference between the square of the optical head signal (used for diameter measurements) and the capacitive head signal (used for cross-section or volume measurements) becomes zero, thus compensating the capacitive head signal for diameter variations and permitting the remaining signal to be used for conclusions about moisture content.

The use of the two measuring elements also permits automatic checking of the measuring head by comparison of individual filtered-out signal components and their testing for plausibility. If one individual component or a combination of such components exhibits an unusual deviation (e.g., unusual drift, decreasing sensitivity) from a predetermined standard deviation, a malfunction of a measuring element is inferred and a changeover is made to the measuring element with the assumed correct measured value. If required, it is also possible for only the disturbed signal component to be switched out of consideration in a measurement evaluation or for an alarm to be triggered.

The signals of the two measuring elements can thus be evaluated in accordance with the present invention in such a way that information can be derived about other parameters, for example about bulk, hairiness, moisture content, extraneous fibers, twist, specific gravity and the like.

Further, the simultaneous use of both types of measuring elements will as a rule result in an increase in the measurement accuracy in that the fluctuations in accuracy of the two systems will at least partially cancel each other out.

It will be appreciated by those o ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. Device for monitoring parameters of a running, thread-like or wire-like elongated test material, comprising:
   means for establishing a measuring gap which provides for passage of the test material, said measuring gap having two side walls each of which is provided with a measuring electrode forming part of a capacitive measuring element for monitoring the cross-section of the test material; and,
   means for optically measuring the test material within said measuring gap, said optical measuring means including an optical measuring element for monitoring the diameter of the test material, said optical measurement element further including a light source arranged on a side of the measuring gap and a photoelectric element positioned to receive light from said light source, the capacitive measuring element and the optical measuring element being formed as part of a common measuring head.

2. Device according to claim 1, wherein the capacitive measuring element and the optical measuring element are integrated on a common carrier.

3. Device according to claim 2, wherein the capacitive measuring element and the optical measuring element are arranged in a common housing.

4. Device according to claim 3, wherein the capacitive measuring element and the optical measuring element are arranged side-by-side in a direction of running of the test material and have spatially separated measuring zones.

5. Device according to claim 2, wherein the capacitive measuring element and the optical measuring element are combined with one another and their measuring zones overlap at least partially.

6. Device according to claim 5, wherein the measuring electrodes of the capacitive measuring element are arranged in a beam path of the optical measuring element.

7. Device according to claim 6, wherein the measuring gap is bounded on both sides by a diffusing screen of said optical measuring element, and wherein the measuring electrodes are supported by these diffusing screens.

8. Device according to claim 7, wherein each measuring electrode is of a lattice or sieve design and is embedded in the diffusing screens.

9. Device according to claim 7, wherein each measuring electrode is of a lattice or sieve design and is coated on one side of the diffusing screens.

10. Device according to claim 7, wherein each measuring electrode is formed by a film layer which is transparent for the optical measuring element.

11. Device according to claim 10, wherein the film layer is formed by a metal layer vapor-deposited on or sprayed onto the diffusing screens.

12. Device according to claim 10, wherein the film layer is formed by a layer of electrically conductive plastic applied to the diffusing screens.

13. Apparatus for monitoring parameters of a running, thread-like or wire-like elongated test material comprising:
   means for establishing a capacitive measuring gap through which a test material passes, said gap establishing means including a first measuring electrode located on a first side of said gap, and a second measuring electrode located on a second side of said gap opposite said first side; and
   means for optically measuring the test material in said capacitive gap, said optical measuring means including a light source located on said first side and a photoelectric element located on said second side.

* * * * *